United States Patent
Barranco-Medina et al.

(10) Patent No.: US 10,954,502 B2
(45) Date of Patent: *Mar. 23, 2021

(54) THROMBIN-THROMBOMODULIN FUSION PROTEINS AS PROTEIN C ACTIVATORS

(71) Applicant: Saint Louis University, St. Louis, MO (US)

(72) Inventors: Sergio Barranco-Medina, Manchester, MO (US); Nicola Pozzi, St. Louis, MO (US); Enrico Di Cera, St. Louis, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/570,582

(22) PCT Filed: Apr. 28, 2016

(86) PCT No.: PCT/US2016/029768
§ 371 (c)(1),
(2) Date: Oct. 30, 2017

(87) PCT Pub. No.: WO2016/176440
PCT Pub. Date: Nov. 3, 2016

(65) Prior Publication Data
US 2018/0127735 A1 May 10, 2018

Related U.S. Application Data

(60) Provisional application No. 62/153,742, filed on Apr. 28, 2015.

(51) Int. Cl.
| | | |
|---|---|---|
| *C12N 9/96* | (2006.01) | |
| *C12N 9/74* | (2006.01) | |
| *C07K 14/745* | (2006.01) | |
| *G01N 33/86* | (2006.01) | |
| *C12Q 1/37* | (2006.01) | |
| *C12Q 1/56* | (2006.01) | |

(52) U.S. Cl.
CPC ........ *C12N 9/6429* (2013.01); *C07K 14/7455* (2013.01); *C12Q 1/37* (2013.01); *C12Q 1/56* (2013.01); *C12Y 304/21005* (2013.01); *C12Y 304/21069* (2013.01); *G01N 33/86* (2013.01); *C07K 2319/00* (2013.01); *C07K 2319/50* (2013.01); *C07K 2319/61* (2013.01); *G01N 2333/7452* (2013.01); *G01N 2333/96461* (2013.01); *G01N 2333/974* (2013.01); *G01N 2800/226* (2013.01)

(58) Field of Classification Search
None
See application file for complete search history.

(56) References Cited

U.S. PATENT DOCUMENTS

| | | | | |
|---|---|---|---|---|
| 7,622,122 | B2 * | 11/2009 | Light | A61P 43/00 424/192.1 |
| 8,343,764 | B2 * | 1/2013 | Abad | C12N 15/8241 435/419 |
| 2008/0286290 | A1 * | 11/2008 | Furusako | A61P 7/00 424/178.1 |
| 2010/0159512 | A1 | 6/2010 | Osther | |
| 2012/0164129 | A1 | 6/2012 | Di Cera et al. | |
| 2013/0052715 | A1 | 2/2013 | Anton et al. | |
| 2016/0160203 | A1 * | 6/2016 | McClain | C12N 9/6429 435/226 |

OTHER PUBLICATIONS

Maruyama et al. (JBC, vol. 260, No. 29, pp. 15432-15438, 1985).*
Adams et al. (Molecular Basis of Thrombomodulin Activation of Slow Thrombin', J. of Thrombosis & Haemost. vo.7, pates 1688-95, 2009).*
Baerga-Ortiz et al., Electrostatic Dependence of the Thrombin-Thrombomodulin Interaction, J. Mol. Biol., 2000, vol. 296, pp. 651-658.
Bode et al., The refined 1.9 A crystal structure of human a-thrombin: interaction with D-Phe_pro_Arg chloromethylketone and significance of the Tyr-Pro-Pro-Trp insertion segment; The EMBO Journal, 1989, vol. 8, No. 11, pp. 3467-3475.
Cantwell et al., Rational Design of a Potent Anticoagulant Thrombin; The Journal of Biological Chemistry, 2000, Issue of Dec. 22, vol. 275, No. 51, pp. 39827-39830.
Chichili et al, Linkers in the structural biology of protein-protein interactions, The Protein Society, 2013, vol. 22, pp. 153-167.
Comp et al., Determination of Functional Levels of Protein C, an Antithrombotic Protein, Using Thrombin-Thrombomodulin Complex, Blood, vol. 63, No. 1, 1984, pp. 15-21.
Dade Behring, Protein C. Reagent, Edition Oct. 2000.
Dang et al., Chromogenic Substrates Selective for Activated Protein C; Blood, vol. 89, pp. 2220-2222.
Marino et al., Engineering Thrombin for Selective Specificity toward Protein C and PAR1; The Journal of Biological Chemistry, 2010, vol. 285, No. 25 pp. 19145-19152.

* cited by examiner

*Primary Examiner* — Hope A Robinson
(74) *Attorney, Agent, or Firm* — Stinson LLP

(57) ABSTRACT

Compositions and methods for regulating the blood coagulation pathway are disclosed. More particularly, the present disclosure relates to thrombin-thrombomodulin fusion proteins, vectors, host cells and methods for preparing the thrombin-thrombomodulin fusion proteins. The present disclosure further relates to methods for measuring protein C in plasma and kits for measuring protein C in plasma.

4 Claims, 1 Drawing Sheet
Specification includes a Sequence Listing.

SEQUENCE LISTING

<160> NUMBER OF SEQ ID NOS: 23

<210> SEQ ID NO 1
<211> LENGTH: 622
<212> TYPE: PRT
<213> ORGANISM: Homo sapiens

<400> SEQUENCE: 1

```
Met Ala His Val Arg Gly Leu Gln Leu Pro Gly Cys Leu Ala Leu Ala
1               5                   10                  15
Ala Leu Cys Ser Leu Val His Ser Gln His Val Phe Leu Ala Pro Gln
            20                  25                  30
Gln Ala Arg Ser Leu Leu Gln Arg Val Arg Arg Ala Asn Thr Phe Leu
        35                  40                  45
Glu Glu Val Arg Lys Gly Asn Leu Glu Arg Glu Cys Val Glu Glu Thr
    50                  55                  60
Cys Ser Tyr Glu Glu Ala Phe Glu Ala Leu Glu Ser Ser Thr Ala Thr
65                  70                  75                  80
Asp Val Phe Trp Ala Lys Tyr Thr Ala Cys Glu Thr Ala Arg Thr Pro
                85                  90                  95
Arg Asp Lys Leu Ala Ala Cys Leu Glu Gly Asn Cys Ala Glu Gly Leu
            100                 105                 110
Gly Thr Asn Tyr Arg Gly His Val Asn Ile Thr Arg Ser Gly Ile Glu
        115                 120                 125
Cys Gln Leu Trp Arg Ser Arg Tyr Pro His Lys Pro Glu Ile Asn Ser
    130                 135                 140
Thr Thr His Pro Gly Ala Asp Leu Gln Glu Asn Phe Cys Arg Asn Pro
145                 150                 155                 160
Asp Ser Ser Thr Thr Gly Pro Trp Cys Tyr Thr Thr Asp Pro Thr Val
                165                 170                 175
Arg Arg Gln Glu Cys Ser Ile Pro Val Cys Gly Gln Asp Gln Val Thr
            180                 185                 190
Val Ala Met Thr Pro Arg Ser Glu Gly Ser Ser Val Asn Leu Ser Pro
        195                 200                 205
Pro Leu Glu Gln Cys Val Pro Asp Arg Gly Gln Gln Tyr Gln Gly Arg
    210                 215                 220
Leu Ala Val Thr Thr His Gly Leu Pro Cys Leu Ala Trp Ala Ser Ala
225                 230                 235                 240
Gln Ala Lys Ala Leu Ser Lys His Gln Asp Phe Asn Ser Ala Val Gln
                245                 250                 255
Leu Val Glu Asn Phe Cys Arg Asn Pro Asp Gly Asp Glu Glu Gly Val
            260                 265                 270
Trp Cys Tyr Val Ala Gly Lys Pro Gly Asp Phe Gly Tyr Cys Asp Leu
        275                 280                 285
Asn Tyr Cys Glu Glu Ala Val Glu Glu Glu Thr Gly Asp Gly Leu Asp
    290                 295                 300
Glu Asp Ser Asp Arg Ala Ile Glu Gly Arg Thr Ala Thr Ser Glu Tyr
305                 310                 315                 320
Gln Thr Phe Phe Asn Pro Arg Thr Phe Gly Ser Gly Glu Ala Asp Cys
                325                 330                 335
Gly Leu Arg Pro Leu Phe Glu Lys Lys Ser Leu Glu Asp Lys Thr Glu
            340                 345                 350
Arg Glu Leu Leu Glu Ser Tyr Ile Asp Gly Arg Ile Val Glu Gly Ser
        355                 360                 365
Asp Ala Glu Ile Gly Met Ser Pro Trp Gln Val Met Leu Phe Arg Lys
    370                 375                 380
Ser Pro Gln Glu Leu Leu Cys Gly Ala Ser Leu Ile Ser Asp Arg Trp
385                 390                 395                 400
Val Leu Thr Ala Ala His Cys Leu Leu Tyr Pro Pro Trp Asp Lys Asn
                405                 410                 415
```

```
Phe Thr Glu Asn Asp Leu Leu Val Arg Ile Gly Lys His Ser Arg Thr
            420                 425                 430
Arg Tyr Glu Arg Asn Ile Glu Lys Ile Ser Met Leu Glu Lys Ile Tyr
        435                 440                 445
Ile His Pro Arg Tyr Asn Trp Arg Glu Asn Leu Asp Arg Asp Ile Ala
    450                 455                 460
Leu Met Lys Leu Lys Lys Pro Val Ala Phe Ser Asp Tyr Ile His Pro
465                 470                 475                 480
Val Cys Leu Pro Asp Arg Glu Thr Ala Ala Ser Leu Leu Gln Ala Gly
                485                 490                 495
Tyr Lys Gly Arg Val Thr Gly Trp Gly Asn Leu Lys Glu Thr Trp Thr
            500                 505                 510
Ala Asn Val Gly Lys Gly Gln Pro Ser Val Leu Gln Val Val Asn Leu
        515                 520                 525
Pro Ile Val Glu Arg Pro Val Cys Lys Asp Ser Thr Arg Ile Arg Ile
    530                 535                 540
Thr Asp Asn Met Phe Cys Ala Gly Tyr Lys Pro Asp Glu Gly Lys Arg
545                 550                 555                 560
Gly Asp Ala Cys Glu Gly Asp Ser Gly Gly Pro Phe Val Met Lys Ser
                565                 570                 575
Pro Phe Asn Asn Arg Trp Tyr Gln Met Gly Ile Val Ser Trp Gly Glu
            580                 585                 590
Gly Cys Asp Arg Asp Gly Lys Tyr Gly Phe Tyr Thr His Val Phe Arg
        595                 600                 605
Leu Lys Lys Trp Ile Gln Lys Val Ile Asp Gln Phe Gly Glu
    610                 615                 620

<210> SEQ ID NO 2
<211> LENGTH: 1389
<212> TYPE: DNA
<213> ORGANISM: Artificial Sequence
<220> FEATURE:
<223> OTHER INFORMATION: Synthetic

<400> SEQUENCE: 2
atgttcctcg cttgccctgg cttctgggtc ctcgtggtcc taggcagcag ctgggcaggc      60
tgggggaacc tagggctga agcagcaaag cttgaagacc aagtagatcc gcggctcatt     120
gatgggaagg tcgacctgtc acctccattg agcagtgtg tccctgatcg ggggcagcag     180 taccagggc gcctggcggt gaccacacat gggctcccct gcctggcctg gccagcgca     240 caggccaagg ccctgagcaa gcaccaggac ttcaactcag ctgtgcagct ggtggagaac     300
ttctgccgca acccagacgg ggatgaggag ggcgtgtggt gctatgtggc cgggaagcct     360
ggcgactttg gtactgcga cctcaactat tgtgaggagg ccgtggagga ggagacagga     420
gatgggctgg atgaggactc agacagggcc atcgaagggc gtaccgccac cagtgagtac     480
cagactttct tcaatccgag gacctttggc tcggagaggg cagactgtgg gctgcgacct     540
ctgttcgaga agaagtcgct ggaggacaaa accgaaagag agctcctgga atcctacatc     600
gacgggcgca ttgtggaggg ctcggatgca gagatcggca tgtcccttg cggtgatg     660 cttttccgga agagtcccca ggagctgctg tgtgggccca gcctcatcag tgaccgctgg     720
gtcctcaccg ccgcccactg cctcctgtac ccgcctggg acaagaactt cacccgagaat     780 gacctttctgg tgcgcattgg caagcactcc gcaccaggt acgagcgaaa cattgaaaag     840
atatccatgt tggaaaagat ctacatccac cccaggtaca actggcggga gaaacctggac    900
```

```
cgggacattg ccctgatgaa gctgaagaag cctgttgcct tcagtgacta cattcaccct    960
gtgtgtctgc ccgacaggga gacggcagcc agcttgctcc aggctggata caaggggcgg   1020
gtgacaggct ggggcaacct gaaggagacg tggacagcca acgttggtaa ggggcagccc   1080
agtgtcctgc aggtggtgaa cctgcccatt gtggagcggc cggtctgcaa ggactccacc   1140
cggatccgca tcactgacaa catgttctgt gctggttaca agcctgatga agggaaacga   1200
ggggatgcct gtgaaggtga cagtggggga ccctttgtca tgaagagccc ctttaacaac   1260
cgctggtacc aaatgggcat cgtctcatgg ggtgaaggct gtgaccggga tgggaaatat   1320
ggcttctaca cacacgtgtt ccgcctgaag aagtggatac agaaggtcat tgatcagttt   1380
ggagagtag                                                           1389
```

<210> SEQ ID NO 3
<211> LENGTH: 462
<212> TYPE: PRT
<213> ORGANISM: Artificial Sequence
<220> FEATURE:
<223> OTHER INFORMATION: Synthetic

<400> SEQUENCE: 3

```
Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asn Pro Arg Thr Phe Gly Ser Gly Glu Ala Asp Cys
                165                 170                 175

Gly Leu Arg Pro Leu Phe Glu Lys Lys Ser Leu Glu Asp Lys Thr Glu
            180                 185                 190

Arg Glu Leu Leu Glu Ser Tyr Ile Asp Gly Arg Ile Val Glu Gly Ser
        195                 200                 205

Asp Ala Glu Ile Gly Met Ser Pro Trp Gln Val Met Leu Phe Arg Lys
    210                 215                 220

Ser Pro Gln Glu Leu Leu Cys Gly Ala Ser Leu Ile Ser Asp Arg Trp
225                 230                 235                 240

Val Leu Thr Ala Ala His Cys Leu Leu Tyr Pro Pro Trp Asp Lys Asn
                245                 250                 255

Phe Thr Glu Asn Asp Leu Leu Val Arg Ile Gly Lys His Ser Arg Thr
            260                 265                 270
```

```
Arg Tyr Glu Arg Asn Ile Glu Lys Ile Ser Met Leu Glu Lys Ile Tyr
            275                 280                 285
Ile His Pro Arg Tyr Asn Trp Arg Glu Asn Leu Asp Arg Asp Ile Ala
        290                 295                 300
Leu Met Lys Leu Lys Lys Pro Val Ala Phe Ser Asp Tyr Ile His Pro
305                 310                 315                 320
Val Cys Leu Pro Asp Arg Glu Thr Ala Ala Ser Leu Leu Gln Ala Gly
                325                 330                 335
Tyr Lys Gly Arg Val Thr Gly Trp Gly Asn Leu Lys Glu Thr Trp Thr
            340                 345                 350
Ala Asn Val Gly Lys Gly Gln Pro Ser Val Leu Gln Val Val Asn Leu
        355                 360                 365
Pro Ile Val Glu Arg Pro Val Cys Lys Asp Ser Thr Arg Ile Arg Ile
    370                 375                 380
Thr Asp Asn Met Phe Cys Ala Gly Tyr Lys Pro Asp Glu Gly Lys Arg
385                 390                 395                 400
Gly Asp Ala Cys Glu Gly Asp Ser Gly Gly Pro Phe Val Met Lys Ser
                405                 410                 415
Pro Phe Asn Asn Arg Trp Tyr Gln Met Gly Ile Val Ser Trp Gly Glu
            420                 425                 430
Gly Cys Asp Arg Asp Gly Lys Tyr Gly Phe Tyr Thr His Val Phe Arg
        435                 440                 445
Leu Lys Lys Trp Ile Gln Lys Val Ile Asp Gln Phe Gly Glu
    450                 455                 460

<210> SEQ ID NO 4
<211> LENGTH: 1389
<212> TYPE: DNA
<213> ORGANISM: Artificial Sequence
<220> FEATURE:
<223> OTHER INFORMATION: Synthetic

<400> SEQUENCE: 4
atgttcctcg cttgccctgg cttctgggtc ctcgtggtcc taggcagcag ctgggcaggc      60
tgggggaacc taggggctga agcagcaaag cttgaagacc aagtagatcc gcggctcatt     120
gatgggaagg tcgacctgtc acctccattg agcagtgtg tccctgatcg ggggcagcag     180
taccaggggc gcctggcggt gaccacacat gggctcccct gcctggcctg gccagcgca     240
caggccaagg ccctgagcaa gcaccaggac ttcaactcag ctgtgcagct ggtggagaac     300
ttctgccgca acccagacgg ggatgaggag gcgtgtggt gctatgtggc cgggaagcct     360
ggcgactttg gtactgcga cctcaactat tgtgaggagg ccgtgaagga ggagacagga     420
gatgggctgg atgaggactc agacagggcc atcgaagggc gtaccgccac cagtgagtac     480
cagactttct tcgacgggag gacctttggc tcgggagagg cagactgtgg gctgcgacct     540
ctgttcgaga gaagtcgct ggaggacaaa accgaaagag agctcctgga atcctcatc     600
gacgggcgca ttgtggaggg ctcggatgca gagatcggca tgtcaccttg gcaggtgatg     660
ctttccgga agagtcccca ggagctgctg tgtgggcca gcctcatcag tgaccgctgg     720
gtcctcaccg ccgcccactg cctcctgtac ccgcccctggg acaagaactt caccgagaat     780
gaccttctgg tgcgcattgg caagcactcc cgcaccaggt acgagcgaaa cattgaaaag     840
atatccatgt tggaaaagat ctacatccac cccaggtaca actggcggga gaacctggac     900
cgggacattg ccctgatgaa gctgaagaag cctgttgcct tcagtgacta cattcaccct     960
gtgtgtctgc ccgacaggga gacggcagcc agcttgctcc aggctggata caagggcggg    1020
```

```
gtgacaggct ggggcaacct gaaggagacg tggacagcca acgttggtaa ggggcagccc    1080
agtgtcctgc aggtggtgaa cctgcccatt gtggagcggc cggtctgcaa ggactccacc    1140
cggatccgca tcactgacaa catgttctgt gctggttaca agcctgatga agggaaacga    1200
ggggatgcct gtgaaggtga cagtggggga cccttttgtca tgaagagccc ctttaacaac    1260
cgctggtacc aaatgggcat cgtctcatgg ggtgaaggct gtgaccggga tgggaaatat    1320
ggcttctaca cacacgtgtt ccgcctgaag aagtggatac agaaggtcat tgatcagttt    1380
ggagagtag                                                            1389
```

<210> SEQ ID NO 5
<211> LENGTH: 462
<212> TYPE: PRT
<213> ORGANISM: Artificial Sequence
<220> FEATURE:
<223> OTHER INFORMATION: Synthetic

<400> SEQUENCE: 5

```
Met Phe Leu Ala Cys Pro Gly Phe Trp Val Leu Val Leu Gly Ser
1               5                   10                  15

Ser Trp Ala Gly Trp Gly Asn Leu Gly Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Thr Glu
            180                 185                 190

Arg Glu Leu Leu Glu Ser Tyr Ile Asp Gly Arg Ile Val Glu Gly Ser
        195                 200                 205

Asp Ala Glu Ile Gly Met Ser Pro Trp Gln Val Met Leu Phe Arg Lys
    210                 215                 220

Ser Pro Gln Glu Leu Leu Cys Gly Ala Ser Leu Ile Ser Asp Arg Trp
225                 230                 235                 240

Val Leu Thr Ala Ala His Cys Leu Leu Tyr Pro Pro Trp Asp Lys Asn
                245                 250                 255

Phe Thr Glu Asn Asp Leu Leu Val Arg Ile Gly Lys His Ser Arg Thr
            260                 265                 270

Arg Tyr Glu Arg Asn Ile Glu Lys Ile Ser Met Leu Glu Lys Ile Tyr
        275                 280                 285
```

```
Ile His Pro Arg Tyr Asn Trp Arg Glu Asn Leu Asp Arg Asp Ile Ala
            290                 295                 300

Leu Met Lys Leu Lys Lys Pro Val Ala Phe Ser Asp Tyr Ile His Pro
305                 310                 315                 320

Val Cys Leu Pro Asp Arg Glu Thr Ala Ala Ser Leu Leu Gln Ala Gly
                325                 330                 335

Tyr Lys Gly Arg Val Thr Gly Trp Gly Asn Leu Lys Glu Thr Trp Thr
            340                 345                 350

Ala Asn Val Gly Lys Gly Gln Pro Ser Val Leu Gln Val Val Asn Leu
        355                 360                 365

Pro Ile Val Glu Arg Pro Val Cys Lys Asp Ser Thr Arg Ile Arg Ile
370                 375                 380

Thr Asp Asn Met Phe Cys Ala Gly Tyr Lys Pro Asp Glu Gly Lys Arg
385                 390                 395                 400

Gly Asp Ala Cys Glu Gly Asp Ser Gly Gly Pro Phe Val Met Lys Ser
                405                 410                 415

Pro Phe Asn Asn Arg Trp Tyr Gln Met Gly Ile Val Ser Trp Gly Glu
            420                 425                 430

Gly Cys Asp Arg Asp Gly Lys Tyr Gly Phe Tyr Thr His Val Phe Arg
        435                 440                 445

Leu Lys Lys Trp Ile Gln Lys Val Ile Asp Gln Phe Gly Glu
450                 455                 460

<210> SEQ ID NO 6
<211> LENGTH: 360
<212> TYPE: DNA
<213> ORGANISM: Artificial Sequence
<220> FEATURE:
<223> OTHER INFORMATION: Synthetic

<400> SEQUENCE: 6
gtggagcccg tggacccgtg cttcgccaac tgcgagtacc agtgccagcc cctgaaccaa      60
actagctacc tctgcgtctg cgccgagggc ttcgcgccca ttccccacga gccgcacagg     120
tgccagatgt tttgcaacca gactgcctgt ccagccgact gcgacccaaa cacccaggct     180
agctgtgagt gccctgaagg ctacatcctg gacgacggtt tcatctgcac ggacatcgac     240
gagtgcgaaa acggcggctt ctgctccggg gtgtgccaca acctcccggg taccttcgag     300
tgcatctgcg ggcccgactc ggcccttgcc cgccacattg gcaccgactg tgactccggc     360

<210> SEQ ID NO 7
<211> LENGTH: 120
<212> TYPE: PRT
<213> ORGANISM: Artificial Sequence
<220> FEATURE:
<223> OTHER INFORMATION: Synthetic

<400> SEQUENCE: 7

Val Glu Pro Val Asp Pro Cys Phe Ala Asn Cys Glu Tyr Gln Cys Gln
1               5                   10                  15

Pro Leu Asn Gln Thr Ser Tyr Leu Cys Val Cys Ala Glu Gly Phe Ala
            20                  25                  30

Pro Ile Pro His Glu Pro His Arg Cys Gln Met Phe Cys Asn Gln Thr
        35                  40                  45

Ala Cys Pro Ala Asp Cys Asp Pro Asn Thr Gln Ala Ser Cys Glu Cys
    50                  55                  60

Pro Glu Gly Tyr Ile Leu Asp Asp Gly Phe Ile Cys Thr Asp Ile Asp
65                  70                  75                  80
```

```
Glu Cys Glu Asn Gly Gly Phe Cys Ser Gly Val Cys His Asn Leu Pro
                85                  90                  95

Gly Thr Phe Glu Cys Ile Cys Gly Pro Asp Ser Ala Leu Ala Arg His
            100                 105                 110

Ile Gly Thr Asp Cys Asp Ser Gly
        115                 120
```

<210> SEQ ID NO 8
<211> LENGTH: 363
<212> TYPE: DNA
<213> ORGANISM: Artificial Sequence
<220> FEATURE:
<223> OTHER INFORMATION: Synthetic

<400> SEQUENCE: 8

```
gtggagcccg tggacccgtg cttcagagcc aactgcgagt accagtgcca gcccctgaac      60
caaactagct acctctgcgt ctgcgccgag ggcttcgcgc ccattcccca cgagccgcac     120
aggtgccaga tgttttgcaa ccagactgcc tgtccagccg actgcgaccc caacacccag     180
gctagctgtg agtgccctga aggctacatc ctggacgacg gtttcatctg cacggacatc     240
gacgagtgcg aaaacggcgg cttctgctcc ggggtgtgcc acaacctccc cggtaccttc     300
gagtgcatct gcgggcccga ctcggccctt gcccgccaca ttggcaccga ctgtgactcc     360
ggc                                                                  363
```

<210> SEQ ID NO 9
<211> LENGTH: 121
<212> TYPE: PRT
<213> ORGANISM: Artificial Sequence
<220> FEATURE:
<223> OTHER INFORMATION: Synthetic

<400> SEQUENCE: 9

```
Val Glu Pro Val Asp Pro Cys Phe Arg Ala Asn Cys Glu Tyr Gln Cys
1               5                   10                  15

Gln Pro Leu Asn Gln Thr Ser Tyr Leu Cys Val Cys Ala Glu Gly Phe
            20                  25                  30

Ala Pro Ile Pro His Glu Pro His Arg Cys Gln Met Phe Cys Asn Gln
        35                  40                  45

Thr Ala Cys Pro Ala Asp Cys Asp Pro Asn Thr Gln Ala Ser Cys Glu
    50                  55                  60

Cys Pro Glu Gly Tyr Ile Leu Asp Asp Gly Phe Ile Cys Thr Asp Ile
65                  70                  75                  80

Asp Glu Cys Glu Asn Gly Gly Phe Cys Ser Gly Val Cys His Asn Leu
                85                  90                  95

Pro Gly Thr Phe Glu Cys Ile Cys Gly Pro Asp Ser Ala Leu Ala Arg
            100                 105                 110

His Ile Gly Thr Asp Cys Asp Ser Gly
        115                 120
```

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

Gly Gly Gly Gly Gly Gly Gly

<210> SEQ ID NO 11
<211> LENGTH: 17
<212> TYPE: PRT
<213> ORGANISM: Artificial Sequence
<220> FEATURE:
<223> OTHER INFORMATION: Synthetic

<400> SEQUENCE: 11

Gly Gly Gly Ser Ser Ser Ala Gly Gly Gly Ser Ser Ser Gly Gly Gly
1               5                   10                  15

Gly

<210> SEQ ID NO 12
<211> LENGTH: 31
<212> TYPE: PRT
<213> ORGANISM: Artificial Sequence
<220> FEATURE:
<223> OTHER INFORMATION: Synthetic

<400> SEQUENCE: 12

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly
            20                  25                  30

<210> SEQ ID NO 13
<211> LENGTH: 41
<212> TYPE: PRT
<213> ORGANISM: Artificial Sequence
<220> FEATURE:
<223> OTHER INFORMATION: Synthetic

<400> SEQUENCE: 13

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly Ala
            20                  25                  30

Ser Ser Ser Gly Ser Ala Gly Ser Ser
        35                  40

<210> SEQ ID NO 14
<211> LENGTH: 55
<212> TYPE: PRT
<213> ORGANISM: Artificial Sequence
<220> FEATURE:
<223> OTHER INFORMATION: Synthetic

<400> SEQUENCE: 14

Gly Gly Gly Ser Ser Ser Ala Gly Gly Gly Ser Ser Ser Gly Gly Gly
1               5                   10                  15

Gly Ser Ser Ser Ala Gly Gly Gly Ser Ser Ser Gly Gly Gly Gly Ala
            20                  25                  30

Ser Ser Ser Gly Ser Ala Gly Ser Ser Gly Gly Gly Ala Ser Ser
        35                  40                  45

Ser Gly Ser Ala Gly Ser Ser
    50                  55

<210> SEQ ID NO 15
<211> LENGTH: 69
<212> TYPE: PRT
<213> ORGANISM: Artificial Sequence
<220> FEATURE:
<223> OTHER INFORMATION: Synthetic

<400> SEQUENCE: 15

Gly Gly Gly Ser Ser Ala Gly Gly Ser Ser Gly Gly Gly
1               5                   10                  15

Gly Ser Ser Ser Ala Gly Gly Ser Ser Gly Gly Gly Ser
            20                  25                  30

Ser Ser Ala Gly Gly Gly Ser Ser Gly Gly Gly Ser Ser Ser
        35                  40                  45

Ala Gly Gly Gly Ser Ser Gly Gly Gly Ala Ser Ser Gly
    50                  55                  60

Ser Ala Gly Ser Ser
65

<210> SEQ ID NO 16
<211> LENGTH: 13
<212> TYPE: PRT
<213> ORGANISM: Artificial Sequence
<220> FEATURE:
<223> OTHER INFORMATION: Synthetic

<400> SEQUENCE: 16

Leu Glu Asp Gln Val Asp Pro Arg Leu Ile Asp Gly Lys
1               5                   10

<210> SEQ ID NO 17
<211> LENGTH: 1845
<212> TYPE: DNA
<213> ORGANISM: Artificial Sequence
<220> FEATURE:
<223> OTHER INFORMATION: Synthetic

<400> SEQUENCE: 17

| | | | | | |
|---|---|---|---|---|---|
| atgttcctcg | cttgccctgg | cttctgggtc | ctcgtggtcc | taggcagcag | ctgggcaggc | 60 |
| tgggggaacc | taggggctga | agcagcaaag | cttgaagacc | aagtagatcc | gcggctcatt | 120 |
| gatgggaagg | tcgacctgtc | acctccattg | gagcagtgtg | tccctgatcg | ggggcagcag | 180 |
| taccagggc | gcctggcggt | gaccacacat | gggctcccct | gcctggcctg | gccagcgca | 240 |
| caggccaagg | ccctgagcaa | gcaccaggac | ttcaactcag | ctgtgcagct | ggtggagaac | 300 |
| ttctgccgca | acccagacgg | ggatgaggag | ggcgtgtggt | gctatgtggc | cgggaagcct | 360 |
| ggcgactttg | gtactgcgca | cctcaactat | tgtgaggagg | ccgtggagga | ggagacagga | 420 |
| gatgggctgg | atgaggactc | agacaggcc | atcgaaggg | gtaccgccac | cagtgagtac | 480 |
| cagactttct | tcgacgggag | gaccttttggc | tcgggagagg | cagactgtgg | gctgcgacct | 540 |
| ctgttcgaga | agaagtcgct | ggaggacaaa | accgaaagag | agctcctgga | atcctacatc | 600 |
| gacgggcgca | ttgtggaggg | ctcggatgca | gagatcggca | tgtcaccttg | gcaggtgatg | 660 |
| cttttccgga | agagtcccca | ggagctgctg | tgtggggcca | gcctcatcag | tgaccgctgg | 720 |
| gtcctcaccg | ccgcccactg | cctcctgtac | ccgccctggg | acaagaactt | caccgagaat | 780 |
| gaccttctgg | tgcgcattgg | caagcactcc | cgcaccaggt | acgagcgaaa | cattgaaaag | 840 |
| atatccatgt | tggaaaagat | ctacatccac | cccaggtaca | actggcggga | gaacctggac | 900 |
| cgggacattg | ccctgatgaa | gctgaagaag | cctgttgcct | tcagtgacta | cattcaccct | 960 |
| gtgtgtctgc | ccgacaggga | gacggcagcc | agcttgctcc | aggctggata | caagggggg | 1020 |
| gtgacaggct | ggggcaacct | gaaggagacg | tggacagcca | acgttggtaa | ggggcagccc | 1080 |

```
agtgtcctgc aggtggtgaa cctgcccatt gtggagcggc cggtctgcaa ggactccacc    1140
cggatccgca tcactgacaa catgttctgt gctggttaca agcctgatga agggaaacga    1200
ggggatgcct gtgaaggtga cagtggggga ccctttgtca tgaagagccc ctttaacaac    1260
cgctggtacc aaatgggcat cgtctcatgg ggtgaaggct gtgaccggga tgggaaatat    1320
ggcttctaca cacacgtgtt ccgcctgaag aagtggatac agaaggtcat tgatcagttt    1380
ggagagggag gtggatcttc ttctgccggt ggtggttcat cttctggtgg aggtggatct    1440
tcttctgccg gtggtggttc atcttctggt ggaggtggag tggagcccgt ggacccgtgc    1500
ttcagagcca actgcgagta ccagtgccag cccctgaacc aaactagcta cctctgcgtc    1560
tgcgccgagg gcttcgcgcc cattccccac gagccgcaca ggtgccagat gttttgcaac    1620
cagactgcct gtccagccga ctgcgacccc aacacccagg ctagctgtga gtgccctgaa    1680
ggctacatcc tggacgacgg tttcatctgc acggacatcg acgagtgcga aaacggcggc    1740
ttctgctccg gggtgtgcca acctcccc ggtaccttcg agtgcatctg cgggcccgac    1800
tcggcccttg cccgccacat tggcaccgac tgtgactccg gctaa                   1845
```

<210> SEQ ID NO 18
<211> LENGTH: 611
<212> TYPE: PRT
<213> ORGANISM: Artificial Sequence
<220> FEATURE:
<223> OTHER INFORMATION: Synthetic

<400> SEQUENCE: 18

```
Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Glu Arg
            180                 185                 190

Glu Leu Leu Glu Ser Tyr Ile Asp Gly Arg Ile Val Glu Gly Ser Asp
        195                 200                 205

Ala Glu Ile Gly Met Ser Pro Trp Gln Val Met Leu Phe Arg Lys Ser
    210                 215                 220

Pro Gln Glu Leu Leu Cys Gly Ala Ser Leu Ile Ser Asp Arg Trp Val
```

```
                225                 230                 235                 240
Leu Thr Ala Ala His Cys Leu Leu Tyr Pro Pro Trp Asp Lys Asn Phe
                    245                 250                 255
Thr Glu Asn Asp Leu Leu Val Arg Ile Gly Lys His Ser Arg Thr Arg
                260                 265                 270
Tyr Glu Arg Asn Ile Glu Lys Ile Ser Met Leu Glu Lys Ile Tyr Ile
            275                 280                 285
His Pro Arg Tyr Asn Trp Arg Glu Asn Leu Asp Arg Asp Ile Ala Leu
        290                 295                 300
Met Lys Leu Lys Lys Pro Val Ala Phe Ser Asp Tyr Ile His Pro Val
305                 310                 315                 320
Cys Leu Pro Asp Arg Glu Thr Ala Ala Ser Leu Leu Gln Ala Gly Tyr
                325                 330                 335
Lys Gly Arg Val Thr Gly Trp Gly Asn Leu Lys Glu Thr Trp Thr Ala
                340                 345                 350
Asn Val Gly Lys Gly Gln Pro Ser Val Leu Gln Val Val Asn Leu Pro
            355                 360                 365
Ile Val Glu Arg Pro Val Cys Lys Asp Ser Thr Arg Ile Arg Ile Thr
        370                 375                 380
Asp Asn Met Phe Cys Ala Gly Tyr Lys Pro Asp Glu Gly Lys Arg Gly
385                 390                 395                 400
Asp Ala Cys Glu Gly Asp Ser Gly Gly Pro Phe Val Met Lys Ser Pro
                405                 410                 415
Phe Asn Asn Arg Trp Tyr Gln Met Gly Ile Val Ser Trp Gly Glu Gly
                420                 425                 430
Cys Asp Arg Asp Gly Lys Tyr Gly Phe Tyr Thr His Val Phe Arg Leu
            435                 440                 445
Lys Lys Trp Ile Gln Lys Val Ile Asp Gln Phe Gly Gly Gly Ser Ser
        450                 455                 460
Ser Ala Gly Gly Gly Ser Ser Ser Gly Gly Gly Ser Ser Ser Ala
465                 470                 475                 480
Gly Gly Gly Ser Ser Ser Gly Gly Gly Val Glu Pro Val Asp Pro
                485                 490                 495
Cys Phe Arg Ala Asn Cys Glu Tyr Gln Cys Gln Pro Leu Asn Gln Thr
                500                 505                 510
Ser Tyr Leu Cys Val Cys Ala Glu Gly Phe Ala Pro Ile Pro His Glu
            515                 520                 525
Pro His Arg Cys Gln Met Phe Cys Asn Gln Thr Ala Cys Pro Ala Asp
        530                 535                 540
Cys Asp Pro Asn Thr Gln Ala Ser Cys Glu Cys Pro Glu Gly Tyr Ile
545                 550                 555                 560
Leu Asp Asp Gly Phe Ile Cys Thr Asp Ile Asp Glu Cys Glu Asn Gly
                565                 570                 575
Gly Phe Cys Ser Gly Val Cys His Asn Leu Pro Gly Thr Phe Glu Cys
                580                 585                 590
Ile Cys Gly Pro Asp Ser Ala Leu Ala Arg His Ile Gly Thr Asp Cys
            595                 600                 605
Asp Ser Gly
        610

<210> SEQ ID NO 19
<211> LENGTH: 444
<212> TYPE: PRT
<213> ORGANISM: Artificial Sequence
```

<220> FEATURE:
<223> OTHER INFORMATION: Synthetic

<400> SEQUENCE: 19

Thr Phe Gly Ser Gly Glu Ala Asp Cys Gly Leu Arg Pro Leu Phe Glu
1               5                   10                  15

Lys Lys Ser Leu Glu Asp Lys Glu Arg Glu Leu Leu Glu Ser Tyr Ile
            20                  25                  30

Asp Gly Arg Ile Val Glu Gly Ser Asp Ala Glu Ile Gly Met Ser Pro
        35                  40                  45

Trp Gln Val Met Leu Phe Arg Lys Ser Pro Gln Glu Leu Leu Cys Gly
    50                  55                  60

Ala Ser Leu Ile Ser Asp Arg Trp Val Leu Thr Ala Ala His Cys Leu
65                  70                  75                  80

Leu Tyr Pro Pro Trp Asp Lys Asn Phe Thr Glu Asn Asp Leu Leu Val
                85                  90                  95

Arg Ile Gly Lys His Ser Arg Thr Arg Tyr Glu Arg Asn Ile Glu Lys
            100                 105                 110

Ile Ser Met Leu Glu Lys Ile Tyr Ile His Pro Arg Tyr Asn Trp Arg
        115                 120                 125

Glu Asn Leu Asp Arg Asp Ile Ala Leu Met Lys Leu Lys Lys Pro Val
    130                 135                 140

Ala Phe Ser Asp Tyr Ile His Pro Val Cys Leu Pro Asp Arg Glu Thr
145                 150                 155                 160

Ala Ala Ser Leu Leu Gln Ala Gly Tyr Lys Gly Arg Val Thr Gly Trp
                165                 170                 175

Gly Asn Leu Lys Glu Thr Trp Thr Ala Asn Val Gly Lys Gly Gln Pro
            180                 185                 190

Ser Val Leu Gln Val Val Asn Leu Pro Ile Val Glu Arg Pro Val Cys
        195                 200                 205

Lys Asp Ser Thr Arg Ile Arg Ile Thr Asp Asn Met Phe Cys Ala Gly
    210                 215                 220

Tyr Lys Pro Asp Glu Gly Lys Arg Gly Asp Ala Cys Glu Gly Asp Ser
225                 230                 235                 240

Gly Gly Pro Phe Val Met Lys Ser Pro Phe Asn Asn Arg Trp Tyr Gln
                245                 250                 255

Met Gly Ile Val Ser Trp Gly Glu Gly Cys Asp Arg Asp Gly Lys Tyr
            260                 265                 270

Gly Phe Tyr Thr His Val Phe Arg Leu Lys Lys Trp Ile Gln Lys Val
        275                 280                 285

Ile Asp Gln Phe Gly Gly Gly Ser Ser Ala Gly Gly Ser Ser
    290                 295                 300

Ser Gly Gly Gly Gly Ser Ser Ala Gly Gly Ser Ser Ser Gly
305                 310                 315                 320

Gly Gly Val Glu Pro Val Asp Pro Cys Phe Arg Ala Asn Cys Glu
                325                 330                 335

Tyr Gln Cys Gln Pro Leu Asn Gln Thr Ser Tyr Leu Cys Val Cys Ala
            340                 345                 350

Glu Gly Phe Ala Pro Ile Pro His Glu Pro His Arg Cys Gln Met Phe
        355                 360                 365

Cys Asn Gln Thr Ala Cys Pro Ala Asp Cys Asp Pro Asn Thr Gln Ala
    370                 375                 380

Ser Cys Glu Cys Pro Glu Gly Tyr Ile Leu Asp Asp Gly Phe Ile Cys
385                 390                 395                 400

```
Thr Asp Ile Asp Glu Cys Glu Asn Gly Gly Phe Cys Ser Gly Val Cys
            405                 410                 415

His Asn Leu Pro Gly Thr Phe Glu Cys Ile Cys Gly Pro Asp Ser Ala
            420                 425                 430

Leu Ala Arg His Ile Gly Thr Asp Cys Asp Ser Gly
            435                 440

<210> SEQ ID NO 20
<211> LENGTH: 1845
<212> TYPE: DNA
<213> ORGANISM: Artificial Sequence
<220> FEATURE:
<223> OTHER INFORMATION: Synthetic

<400> SEQUENCE: 20
atgttcctcg cttgccctgg cttctgggtc ctcgtggtcc taggcagcag ctgggcaggc      60
tgggggaacc tagggctga agcagcaaag cttgaagacc aagtagatcc gcggctcatt     120
gatgggaagg tcgacctgtc acctccattg agcagtgtg tccctgatcg ggggcagcag     180
taccaggggc gcctggcggt gaccacacat gggctcccct gcctggcctg gccagcgca     240 caggccaagg ccctgagcaa gcaccaggac ttcaactcag ctgtgcagct ggtggagaac    300
ttctgccgca acccagacgg ggatgaggag gcgtgtggt gctatgtggc cgggaagcct    360
ggcgactttg ggtactgcga cctcaactat tgtgaggagg ccgtggagga ggagacagga    420
gatgggctgg atgaggactc agacagggcc atcgaagggc gtaccgccac cagtgagtac    480
cagactttct tcgacgggag gaccttggc tcgggagagg cagactgtgg gctgcgacct    540
ctgttcgaga gaagtcgct ggaggacaaa accgaaagag agctcctgga atcctacatc    600
gacgggcgca ttgtggaggg ctcggatgca gagatcggca tgtcaccttg gcaggtgatg    660 ctttccgga agagtcccca ggagctgctg tgtggggcca gcctcatcag tgaccgctgg    720
gtcctcaccg ccgcccactg cctcctgtac ccgccctggg acaagaactt caccgagaat    780
gaccttctgg tgcgcattgg caagcactcc cgcaccaggt acgagcgaaa cattgaaaag    840
atatccatgt tggaaaagat ctacatccac cccaggtaca actggcggga gaacctggac    900
cgggacattg ccctgatgaa gctgaagaag cctgttgcct tcagtgacta cattcaccct    960
gtgtgtctgc ccgacaggga gacggcagcc agcttgctcc aggctggata caagggcgg    1020 gtgacaggct ggggcaacct gaaggagacg tggacagcca cgttggtaa ggggcagccc    1080 agtgtcctgc agtggtgaa cctgcccatt gtggagcggc cggtctgcaa ggactccacc    1140
cggatccgca tcactgacaa catgttctgt gctggttaca gcctgatga agggaaacga    1200 ggggatgcct gtgaaggtga cagtgggga ccctttgtca tgaagagccc ctttaacaac    1260
cgctggtacc aaatgggcat cgtctcagcg ggtgcaggct gtgaccggga tgggaaatat    1320
ggcttctaca cacacgtgtt ccgcctgaag aagtggatac agaaggtcat tgatcagttt    1380
ggagagggag gtggatcttc ttctgccggt ggtggttcat cttctggtgg aggtggatct    1440
tcttctgccg gtggtggttc atcttctggt ggaggtggag tggagcccgt ggaccgtgc    1500 ttcagagcca actgcgagta ccagtgccag cccctgaacc aaactagcta cctctgcgtc    1560
tgcgccgagg gcttcgcgcc cattccccac gagccgcaca ggtgccagat gttttgcaac    1620
cagactgcct gtccagccga ctgcgacccc aacacccagg ctagctgtga gtgccctgaa    1680
ggctacatcc tggacgacgg tttcatctgc acggacatcg acgagtgcga aaacggcggc    1740
ttctgctccg gggtgtgcca caacctcccc ggtaccttcg agtgcatctg cgggcccgac    1800
```
tcggcccttg cccgccacat tggcaccgac tgtgactccg gctaa        1845

<210> SEQ ID NO 21
<211> LENGTH: 611
<212> TYPE: PRT
<213> ORGANISM: Artificial Sequence
<220> FEATURE:
<223> OTHER INFORMATION: Synthetic

<400> SEQUENCE: 21

Met Phe Leu Ala Cys Pro Gly Phe Trp Val Leu Val Val Leu Gly Ser
1               5                   10                  15

Ser Trp Ala Gly Trp Gly Asn Leu Gly Ala Glu Ala Ala Lys Leu Glu
            20                  25                  30

Asp Gln Val Asp Pro Arg Leu Ile Asp Gly Lys Val Asp Leu Ser Pro
        35                  40                  45

Pro Leu Glu Gln Cys Val Pro Asp Arg Gly Gln Gln Tyr Gln Gly Arg
    50                  55                  60

Leu Ala Val Thr Thr His Gly Leu Pro Cys Leu Ala Trp Ala Ser Ala
65                  70                  75                  80

Gln Ala Lys Ala Leu Ser Lys His Gln Asp Phe Asn Ser Ala Val Gln
                85                  90                  95

Leu Val Glu Asn Phe Cys Arg Asn Pro Asp Gly Asp Glu Glu Gly Val
            100                 105                 110

Trp Cys Tyr Val Ala Gly Lys Pro Gly Asp Phe Gly Tyr Cys Asp Leu
        115                 120                 125

Asn Tyr Cys Glu Glu Ala Val Glu Glu Thr Gly Asp Gly Leu Asp
    130                 135                 140

Glu Asp Ser Asp Arg Ala Ile Glu Gly Arg Thr Ala Thr Ser Glu Tyr
145                 150                 155                 160

Gln Thr Phe Phe Asp Gly Arg Thr Phe Gly Ser Gly Glu Ala Asp Cys
                165                 170                 175

Gly Leu Arg Pro Leu Phe Glu Lys Lys Ser Leu Glu Asp Lys Glu Arg
            180                 185                 190

Glu Leu Leu Glu Ser Tyr Ile Asp Gly Arg Ile Val Glu Gly Ser Asp
        195                 200                 205

Ala Glu Ile Gly Met Ser Pro Trp Gln Val Met Leu Phe Arg Lys Ser
    210                 215                 220

Pro Gln Glu Leu Leu Cys Gly Ala Ser Leu Ile Ser Asp Arg Trp Val
225                 230                 235                 240

Leu Thr Ala Ala His Cys Leu Leu Tyr Pro Pro Trp Asp Lys Asn Phe
                245                 250                 255

Thr Glu Asn Asp Leu Leu Val Arg Ile Gly Lys His Ser Arg Thr Arg
            260                 265                 270

Tyr Glu Arg Asn Ile Glu Lys Ile Ser Met Leu Glu Lys Ile Tyr Ile
        275                 280                 285

His Pro Arg Tyr Asn Trp Arg Glu Asn Leu Asp Arg Asp Ile Ala Leu
    290                 295                 300

Met Lys Leu Lys Lys Pro Val Ala Phe Ser Asp Tyr Ile His Pro Val
305                 310                 315                 320

Cys Leu Pro Asp Arg Glu Thr Ala Ala Ser Leu Leu Gln Ala Gly Tyr
                325                 330                 335

Lys Gly Arg Val Thr Gly Trp Gly Asn Leu Lys Glu Thr Trp Thr Ala
            340                 345                 350

```
Asn Val Gly Lys Gly Gln Pro Ser Val Leu Gln Val Asn Leu Pro
            355                 360                 365

Ile Val Glu Arg Pro Val Cys Lys Asp Ser Thr Arg Ile Arg Ile Thr
    370                 375                 380

Asp Asn Met Phe Cys Ala Gly Tyr Lys Pro Asp Glu Gly Lys Arg Gly
385                 390                 395                 400

Asp Ala Cys Glu Gly Asp Ser Gly Gly Pro Phe Val Met Lys Ser Pro
                405                 410                 415

Phe Asn Asn Arg Trp Tyr Gln Met Gly Ile Val Ser Ala Gly Ala Gly
            420                 425                 430

Cys Asp Arg Asp Gly Lys Tyr Gly Phe Tyr Thr His Val Phe Arg Leu
        435                 440                 445

Lys Lys Trp Ile Gln Lys Val Ile Asp Gln Phe Gly Gly Gly Ser Ser
    450                 455                 460

Ser Ala Gly Gly Gly Ser Ser Gly Gly Gly Ser Ser Ser Ala
465                 470                 475                 480

Gly Gly Gly Ser Ser Gly Gly Gly Val Glu Pro Val Asp Pro
                485                 490                 495

Cys Phe Arg Ala Asn Cys Glu Tyr Gln Cys Gln Pro Leu Asn Gln Thr
                500                 505                 510

Ser Tyr Leu Cys Val Cys Ala Glu Gly Phe Ala Pro Ile Pro His Glu
            515                 520                 525

Pro His Arg Cys Gln Met Phe Cys Asn Gln Thr Ala Cys Pro Ala Asp
        530                 535                 540

Cys Asp Pro Asn Thr Gln Ala Ser Cys Glu Cys Pro Glu Gly Tyr Ile
545                 550                 555                 560

Leu Asp Asp Gly Phe Ile Cys Thr Asp Ile Asp Glu Cys Glu Asn Gly
                565                 570                 575

Gly Phe Cys Ser Gly Val Cys His Asn Leu Pro Gly Thr Phe Glu Cys
            580                 585                 590

Ile Cys Gly Pro Asp Ser Ala Leu Ala Arg His Ile Gly Thr Asp Cys
        595                 600                 605

Asp Ser Gly
    610

<210> SEQ ID NO 22
<211> LENGTH: 444
<212> TYPE: PRT
<213> ORGANISM: Artificial Sequence
<220> FEATURE:
<223> OTHER INFORMATION: Synthetic

<400> SEQUENCE: 22

Thr Phe Gly Ser Gly Glu Ala Asp Cys Gly Leu Arg Pro Leu Phe Glu
1               5                   10                  15

Lys Lys Ser Leu Glu Asp Lys Glu Arg Glu Leu Leu Glu Ser Tyr Ile
            20                  25                  30

Asp Gly Arg Ile Val Glu Gly Ser Asp Ala Glu Ile Gly Met Ser Pro
        35                  40                  45

Trp Gln Val Met Leu Phe Arg Lys Ser Pro Gln Glu Leu Leu Cys Gly
    50                  55                  60

Ala Ser Leu Ile Ser Asp Arg Trp Val Leu Thr Ala Ala His Cys Leu
65                  70                  75                  80

Leu Tyr Pro Pro Trp Asp Lys Asn Phe Thr Glu Asn Asp Leu Leu Val
                85                  90                  95
```

```
Arg Ile Gly Lys His Ser Arg Thr Arg Tyr Glu Arg Asn Ile Glu Lys
                100                 105                 110

Ile Ser Met Leu Glu Lys Ile Tyr Ile His Pro Arg Tyr Asn Trp Arg
            115                 120                 125

Glu Asn Leu Asp Arg Asp Ile Ala Leu Met Lys Leu Lys Lys Pro Val
        130                 135                 140

Ala Phe Ser Asp Tyr Ile His Pro Val Cys Leu Pro Asp Arg Glu Thr
145                 150                 155                 160

Ala Ala Ser Leu Leu Gln Ala Gly Tyr Lys Gly Arg Val Thr Gly Trp
                165                 170                 175

Gly Asn Leu Lys Glu Thr Trp Thr Ala Asn Val Gly Lys Gly Gln Pro
            180                 185                 190

Ser Val Leu Gln Val Val Asn Leu Pro Ile Val Glu Arg Pro Val Cys
        195                 200                 205

Lys Asp Ser Thr Arg Ile Arg Ile Thr Asp Asn Met Phe Cys Ala Gly
210                 215                 220

Tyr Lys Pro Asp Glu Gly Lys Arg Gly Asp Ala Cys Glu Gly Asp Ser
225                 230                 235                 240

Gly Gly Pro Phe Val Met Lys Ser Pro Phe Asn Asn Arg Trp Tyr Gln
                245                 250                 255

Met Gly Ile Val Ser Ala Gly Ala Gly Cys Asp Arg Asp Gly Lys Tyr
            260                 265                 270

Gly Phe Tyr Thr His Val Phe Arg Leu Lys Lys Trp Ile Gln Lys Val
        275                 280                 285

Ile Asp Gln Phe Gly Gly Ser Ser Ser Ala Gly Gly Ser Ser Ser Ser
290                 295                 300

Ser Gly Gly Gly Gly Ser Ser Ser Ala Gly Gly Ser Ser Ser Gly
305                 310                 315                 320

Gly Gly Gly Val Glu Pro Val Asp Pro Cys Phe Arg Ala Asn Cys Glu
                325                 330                 335

Tyr Gln Cys Gln Pro Leu Asn Gln Thr Ser Tyr Leu Cys Val Cys Ala
            340                 345                 350

Glu Gly Phe Ala Pro Ile Pro His Glu Pro His Arg Cys Gln Met Phe
        355                 360                 365

Cys Asn Gln Thr Ala Cys Pro Ala Asp Cys Asp Pro Asn Thr Gln Ala
370                 375                 380

Ser Cys Glu Cys Pro Glu Gly Tyr Ile Leu Asp Asp Gly Phe Ile Cys
385                 390                 395                 400

Thr Asp Ile Asp Glu Cys Glu Asn Gly Gly Phe Cys Ser Gly Val Cys
                405                 410                 415

His Asn Leu Pro Gly Thr Phe Glu Cys Ile Cys Gly Pro Asp Ser Ala
            420                 425                 430

Leu Ala Arg His Ile Gly Thr Asp Cys Asp Ser Gly
        435                 440

<210> SEQ ID NO 23
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: Boc-protected
<222> LOCATION: (1)..(1)
<220> FEATURE:
<221> NAME/KEY: 7-amido-4-methylcoumarin
<222> LOCATION: (4)..(4)
```

```
<400> SEQUENCE: 23

Leu Ser Thr Arg
1
```

THROMBIN-THROMBOMODULIN FUSION PROTEINS AS PROTEIN C ACTIVATORS

CROSS-REFERENCE TO RELATED APPLICATIONS

This application claims priority to International Publication Number WO 2016/176440 A2, filed on Nov. 3, 2016, which claims the benefit to U.S. Provisional Application No. 62/153,742, filed Apr. 28, 2015, each of which is hereby incorporated by reference in its entirety.

STATEMENT REGARDING FEDERALLY SPONSORED RESEARCH OR DEVELOPMENT

This invention was made with government support under HL49413, HL73813 and HL112303 awarded by the National Heart Lung and Blood Institute. The Government has certain rights in the invention.

STATEMENT IN SUPPORT FOR FILING A SEQUENCE LISTING

A paper copy of the Sequence Listing and a computer readable form of the Sequence Listing containing the file named "SLU14016_ST25.txt", which is 47,665 bytes in size (as measured in MICROSOFT WINDOWS EXPLORER), are provided herein and are herein incorporated by reference. This Sequence Listing consists of SEQ ID NOs:1-23.

BACKGROUND OF THE DISCLOSURE

The present disclosure relates generally to compositions and methods for regulating the blood coagulation pathway. More particularly, the present disclosure relates to thrombin-thrombomodulin fusion proteins, vectors, host cells and methods for preparing the thrombin-thrombomodulin fusion proteins. The present disclosure further relates to methods for measuring protein C in plasma and kits for measuring protein C in plasma.

Protein C is a vitamin K dependent protein that circulates in the blood as a zymogen at a concentration of about 4-5 µg/ml (60-80 nM). The protein C zymogen is activated when it binds to thrombin, which works in concert with the cofactor thrombomodulin on the surface of endothelial cells. Activated protein C (aPC) contains a serine protease domain that functions as an anticoagulant that shuts down the coagulation cascade through a feedback mechanism involving the proteolytic inactivation of factor Va and factor VIIIa.

Thrombin (coagulation factor II, EC 3.4.21.5) is a serine protease also involved in the coagulation cascade. Thrombin is formed by the proteolytic cleavage of prothrombin. Thrombin promotes coagulation by converting factor XI to factor XIa, factor VIII to factor VIIIa, factor V to factor Va, factor XIII to factor XIIIa, and soluble fibrinogen into insoluble strands of fibrin. The production of thrombin in vivo occurs through a series of intermediate forms, including prothrombin, prethrombin-1, and prethrombin-2. Each step involves a highly regulated cleavage of the precursor form of thrombin, until mature thrombin is produced. Mature thrombin is formed of two polypeptide chains, the A chain and the B chain, with a disulfide bond between the A and the B chain, and can be produced by cleavage of prethrombin-2 at a specific site.

Thrombomodulin is an integral membrane protein expressed on the surface of endothelial cells and serves as a cofactor for thrombin. The binding of thrombin and thrombomodulin results in the activation of protein C, which then degrades clotting factors Va and VIIIa. Thus, the formation of the thrombin-thrombomodulin complex and activation of protein C promotes the inactivation of the coagulation cascade.

The protein C pathway is the most potent and effective anticoagulant system in vivo. Therefore, congenital or acquired protein C deficiency is an established risk factor of venous thrombosis. Accordingly, there exists a need to develop anticoagulant/antithrombotic agents, methods for the activation of protein C and methods for detecting protein C.

BRIEF DESCRIPTION OF THE DISCLOSURE

The present disclosure is generally directed to compositions and methods for regulating the blood coagulation pathway. More particularly, the present disclosure relates to thrombin-thrombomodulin fusion proteins, vectors, host cells and methods for preparing the thrombin-thrombomodulin fusion proteins. The present disclosure further relates to methods for measuring protein C in plasma and kits for measuring protein C in plasma.

In one aspect, the present disclosure is directed to a thrombin-thrombomodulin fusion protein comprising a thrombin domain and a thrombomodulin domain.

In another aspect, the present disclosure is directed to a vector comprising a nucleic acid encoding a thrombin-thrombomodulin fusion protein, wherein the thrombin-thrombomodulin fusion protein comprises a thrombin domain and a thrombomodulin domain.

In another aspect, the present disclosure is directed to a host cell comprising a vector, wherein the vector comprises a nucleic acid encoding a thrombin-thrombomodulin fusion protein that comprises a thrombin domain and a thrombomodulin domain.

In another aspect, the present disclosure is directed to a measuring protein C activity. The method comprises incubating a plasma sample with a thrombin-thrombomodulin fusion protein in a first reaction mixture; adding a substrate of activated protein C to form a second reaction mixture; and analyzing the second reaction mixture.

In another aspect, the present disclosure is directed to a measuring protein C activity. The method comprises contacting a plasma sample with a thrombin-thrombomodulin fusion protein and a phosphatide reagent to form a first reaction mixture; adding calcium to the first reaction mixture to form a second reaction mixture; and analyzing the second reaction mixture.

In another embodiment, the present disclosure is directed to a kit for measuring protein C in plasma. The kit comprises a thrombin-thrombomodulin fusion protein and a protein C substrate, wherein the protein C substrate is specific for activated protein C.

In accordance with the present disclosure, thrombin-thrombomodulin fusion proteins and uses of the thrombin-thrombomodulin fusion proteins have been discovered that allow for regulating the protein C pathway and for measuring protein C in plasma. The methods of the present disclosure have a broad and significant impact, as they provide innovative agents that function as natural activators of protein C and agents that function to detect protein C. PROTAC® is currently the gold standard diagnostic for Protein C deficiency and is also used to detect factor V Leiden mutation. PROTAC® is made from a harmful toxin extracted from venom of bred Southern Copperhead snakes.

The snake venom is extracted in low-yield, is difficult to produce and standardize, is unstable and can non-specifically activate protein C.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figures 1A, 1B, 1C:
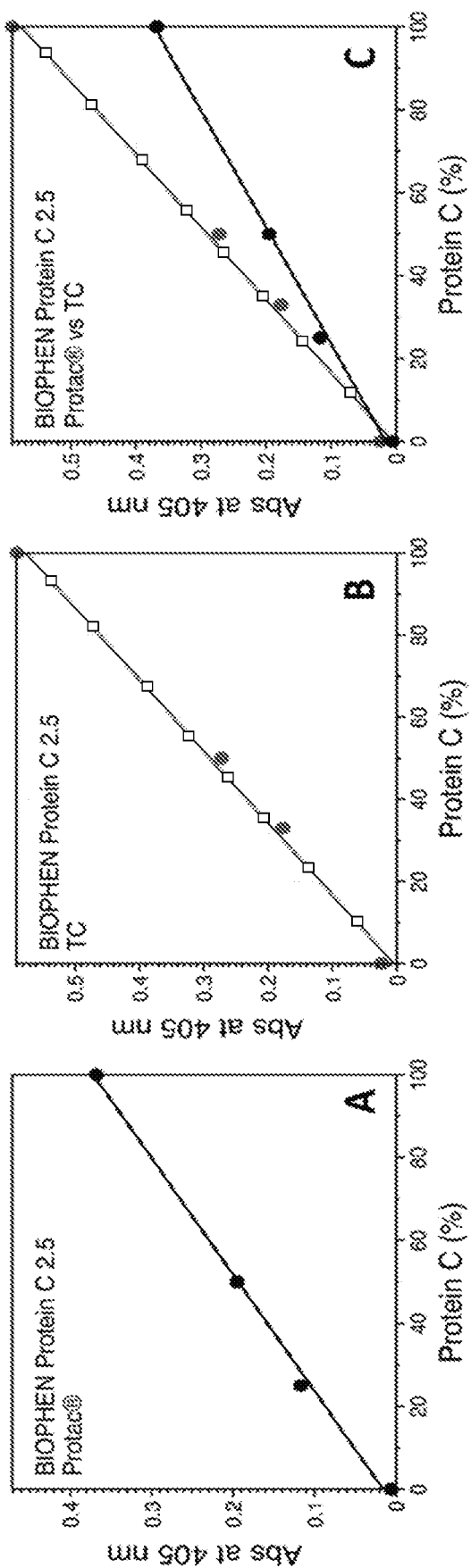
FIG. 1A is a graph depicting the protein C level in citrated plasma using PROTAC® to activate protein C as described in Example 1.
FIG. 1B is a graph depicting the protein C level in citrated plasma using a thrombin-thrombomodulin fusion protein to activate protein C as described in Example 1.
FIG. 1C is a graph depicting a direct comparison between levels of protein C in citrated plasma that was activated using PROTAC® and using a thrombin-thrombomodulin fusion protein as described in Example 1.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

Thrombin-Thrombomodulin Fusion Proteins

In one aspect, the present disclosure is directed to thrombin-thrombomodulin fusion proteins. The thrombin-thrombomodulin fusion protein includes a thrombin domain and a thrombomodulin domain.

The thrombin domain can be a full-length thrombin polypeptide, a preprothrombin polypeptide, a prothrombin polypeptide, a prethrombin 1 polypeptide, a prethrombin 2 polypeptide, a thrombin A chain, a thrombin B chain, and combinations thereof. A particularly suitable thrombin domain is prethrombin 1. The preprothrombin amino acid sequence (from UniProtKB database accession number P00734) represents the full thrombin polypeptide as it is initially expressed. Amino acids 1-24 of SEQ ID NO:1 are the signal peptide, and amino acids 25-43 of SEQ ID NO:1 are a propeptide that is removed to form prothrombin (amino acids 44-622 of SEQ ID NO:1). Amino acids 44-198 of SEQ ID NO:1 are removed when prothrombin is cleaved by thrombin to form prethrombin-1 (amino acids 199-622 of SEQ ID NO:1). Amino acids 199-327 of SEQ ID NO:1 are removed when prethrombin-1 is cleaved by activated factor X (Xa) (or other enzymes) to form prethrombin-2 (amino acids 328-622 of SEQ ID NO:1). Finally, prethrombin-2 is cleaved by Xa to form the A chain (also called the light chain) (amino acids 328-363 of SEQ ID NO:1), and the B chain (also called the heavy chain) (amino acids 364-622 of SEQ ID NO:1) of mature thrombin.

A suitable thrombin domain can have a nucleotide sequence of SEQ ID NO:2. A suitable thrombin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:2. Another suitable thrombin domain can have a nucleotide sequence of SEQ ID NO:4. A suitable thrombin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:4. SEQ ID NO:4 includes an ecarin cleavage site encoded by the nucleotides located at positions 493-501 of SEQ ID NO:4.

Percent identity of two sequences can be determined by aligning the sequences for optimal comparison. For example, gaps can be introduced in the sequence of a first nucleic acid sequence for optimal alignment with the second nucleic acid sequence. The same can be done for optimal alignment of amino acid sequences. The nucleotides or amino acid residues at corresponding positions are then compared. When a position in the first sequence is occupied by the same nucleotide or amino acid as at the corresponding position in the second sequence, the nucleic acids or amino acids are identical at that position. The percent identity between the two sequences is a function of the number of identical nucleotides or amino acids shared by the sequences. Hence, percent identity=[number of identical nucleotides/total number of overlapping positions]×100 or percent identity=[number of identical amino acids/total number of overlapping positions]×100. The percentage of sequence identity can be calculated according to this formula by comparing two optimally aligned sequences being compared, determining the number of positions at which the identical nucleic acid or amino acid occurs in both sequences to yield the number of matched positions (the "number of identical positions" in the formula above), dividing the number of matched positions by the total number of positions being compared (the "total number of overlapping positions" in the formula above), and multiplying the result by 100 to yield the percent sequence identity. In this comparison, the sequences can be the same length or may be different in length. Optimal alignment of sequences for determining a comparison window can be conducted by the local homology algorithm of Smith and Waterman (1981), by the homology alignment algorithm of Needleman and Wunsh (1972), by the search for similarity via the method of Pearson and Lipman (1988), by computerized implementations of these algorithms (GAP, BESTFIT, FASTA and TFASTA in the Wisconsin Genetics Software Package Release 7.0, Genetic Computer Group, 575, Science Drive, Madison, Wis.), or by inspection.

A suitable thrombin domain can have an amino acid sequence of SEQ ID NO:3. A suitable thrombin domain can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:3. Another suitable thrombin domain can have an amino acid sequence of SEQ ID NO:5. A suitable thrombin domain can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:5. SEQ ID NO:5 includes an ecarin cleavage site located at amino acid residues 165-167 of SEQ ID NO:5.

The thrombin domain can further include a thrombin variant. The double thrombin mutant referred to as W215A/E217A thrombin (or WE-thrombin) is constructed by combining the two single mutations W215A and E217A in the human thrombin molecule (as described in Cantwell and Di Cera, J. Biol. Chem. 2000; 275:39827-39830, which is incorporated by reference in its entirety). W215A and E217A refer to amino acid residue positions in the thrombin amino acid residue sequence using the position numbers as described in Bode et al. (EMBO J 1989; 8(11):3467-3475, which is incorporated by reference in its entirety) that corresponds to amino acids 590 and 592 of SEQ ID NO: 1, respectively. Another suitable thrombin variant can be a WE thrombin variant of SEQ ID NO:3 in which the tryptophan (single amino acid letter code W) residue at 430 of SEQ ID NO:3 is substituted with an alanine ($W_{430} \rightarrow A_{430}$) and the glutamic acid (single amino acid letter code E) residue at 432 is substituted with an alanine ($E_{432} \rightarrow A_{432}$). Another suitable thrombin variant can be a WE thrombin variant of SEQ ID NO:5 in which the tryptophan (single amino acid letter code W) residue at 430 of SEQ ID NO:5 is substituted with an alanine ($W_{430} \rightarrow A_{430}$) and the glutamic acid (single amino acid letter code E) residue at 432 is substituted with an alanine ($E_{432} \rightarrow A_{432}$). The human thrombin referred to as E-WE-thrombin is WE-thrombin that has been produced in *E. coli* (US Patent Application Publication 2012/0164129 A1). WE thrombin variants have enhanced protein C activating properties, and reduced fibrinogen-cleaving activity, making them highly anticoagulant thrombins. Other suitable thrombin variants are described in a large number of thrombin polypeptide variants have been characterized in Marino et al., (J. Biol. Chem. 2010; 285(25):19145-19152), which is incorporated by reference in its entirety. The activity of thrombin variants can be analyzed using variety of in vitro assays including, for example, cleavage of prothrombin, cleavage of fibrinogen, and cleavage of fibrin; the activation of protein C, and the interaction with PARI (Cantwell and Di Cera, J. Biol. Chem. 2000; 275(51): 39827-39830). Anticoagulant effects of thrombin variants can also be determined using in vivo assays in experimental animals.

The thrombomodulin domain can be a full-length thrombomodulin protein. A particularly suitable thrombomodulin domain can be thrombomodulin's epidermal growth factor-like domains 456 (TM456). A particularly suitable thrombomodulin domain can have a nucleotide sequence of SEQ ID NO:6 encoding thrombomodulin's epidermal growth factor-like domains 456 (TM456). A suitable thrombomodulin domain can have a nucleotide sequence at least 80%, at least 85%, at least 90%, at least 91%, at least 92%, at least 93%, at least 94%, at least 95%, at least 96%, at least 97%, at least 98%, or at least 99% identical to SEQ ID NO:6.

A particularly suitable thrombomodulin domain can be thrombomodulin's epidermal growth factor-like domains 456 (TM456) having an amino acid sequence of SEQ ID NO:7. A suitable thrombomodulin domain using thrombomodulin's epidermal growth factor-like domains 456 (TM456) can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:7.

Another suitable thrombomodulin domain can be thrombomodulin's epidermal growth factor-like domains 456 (TM456) as encoded by SEQ ID NO:8. A suitable thrombomodulin domain can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:8.

Another suitable thrombomodulin domain can be thrombomodulin's epidermal growth factor-like domains 456 (TM456) having an amino acid sequence of SEQ ID NO:9. A suitable thrombomodulin domain using thrombomodulin's epidermal growth factor-like domains 456 (TM456) can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:9.

The thrombin-thrombomodulin fusion protein can further include at least one linker. A linker functions to couple the thrombin domain to the thrombomodulin domain and to provide distance between the thrombin domain and the thrombomodulin domain. Suitable linkers include, for example, peptide linkers, chemical linkers, and combinations thereof. Particularly suitable peptide linkers are shown in Table 1.

TABLE 1

Linker Sequences.

| Linker Name | Amino Acid Sequence | SEQ ID NO: |
|---|---|---|
| L7 | GGGGGGG | 10 |
| L17 | GGGSSSAGGGSSSGGGG | 11 |
| L31 | GGGSSSAGGGSSSGGGGSSSAGGGSSSGGGG | 12 |
| L41 | GGGSSSAGGGSSSGGGGSSSAGGGSSSGGGGASSSGSAGSS | 13 |
| L55 | GGGSSSAGGGSSSGGGGSSSAGGGSSSGGGGASSSGSAGSSGGGGASSSGSAGSS | 14 |
| L69 | GGGSSSAGGGSSSGGGGSSSAGGGSSSGGGGSSSAGGSGSSSGAGGGSSSGGGGASSSGSAGSS | 15 |

The thrombin-thrombomodulin fusion protein can further include a tag. Suitable tags can be purification tags and labels. Suitable purification tags can be histidine tags and HPC4 tags. A particularly suitable HPC4 tag is an HPC4 epitope tag having the amino acid sequence LEDQVDPR-LIDGK (SEQ ID NO:16).

The thrombin-thrombomodulin fusion protein can further include at least one restriction site. Restriction sites can be incorporated into the thrombin-thrombomodulin fusion protein for purification or other purposes. A particularly suitable restriction site can be at least one ecarin restriction site. Ecarin is a snake venom-derived protease isolated from *Echis carinatu*. The ecarin cleavage site is arginine-isoleucine.

The thrombin-thrombomodulin fusion protein can further include signal peptides or lack them, depending on whether it is desirable for the thrombin-thrombomodulin fusion protein to be exported from the host cell cytoplasm into the periplasm, or to be retained in the cytoplasm, respectively.

The thrombin-thrombomodulin fusion protein can further be glycosylated or unglycosylated.

A particularly suitable thrombin-thrombomodulin fusion protein is encoded by SEQ ID NO:17. Other particularly suitable thrombin-thrombomodulin fusion proteins can have nucleic acid sequence at least 80%, at least 85%, at least 90%, at least 91%, at least 92%, at least 93%, at least 94%, at least 95%, at least 96%, at least 97%, at least 98%, or at least 99% identical to SEQ ID NO:17. A particularly suitable thrombin-thrombomodulin fusion protein has an amino acid sequence of SEQ ID NO:18. Other particularly suitable thrombin-thrombomodulin fusion proteins can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:18. The polypeptide of SEQ ID NO:18 can be treated with ecarin to remove amino acid residues 1-167 to form the final product representing the "active" thrombin-thrombomodulin fusion protein containing the thrombin domain and the thrombomodulin domain. SEQ ID NO:19 is a particularly suitable active thrombin-thrombomodulin fusion protein.

Another particularly suitable thrombin-thrombomodulin fusion protein is encoded by a nucleic acid sequence of SEQ ID NO:20. SEQ ID NO:20 encodes a thrombin-thrombomodulin fusion protein that further includes the WE thrombin double mutation described herein. In particular, SEQ ID NO:20 contains the codon GCG at nucleotides 1288-1290 to encode an alanine and a codon GCA at nucleotides 1294-1296 to encode an alanine. Other particularly suitable thrombin-thrombomodulin fusion proteins can have nucleic acid sequence at least 80%, at least 85%, at least 90%, at least 91%, at least 92%, at least 93%, at least 94%, at least 95%, at least 96%, at least 97%, at least 98%, or at least 99% identical to SEQ ID NO:20, but which includes the WE thrombin double mutation (codon GCG at nucleotides 1288-1290 to encode an alanine and a codon GCA at nucleotides 1294-1296 to encode an alanine).

Another particularly suitable thrombin-thrombomodulin fusion protein includes the amino acid sequence of SEQ ID NO:21. SEQ ID NO:21 represents an example of a thrombin-thrombomodulin fusion protein that further includes the WE thrombin double mutation described herein. The double mutation results from a substitution of tryptophan (single letter amino acid code W) at residue 429 of SEQ ID NO:21 to an alanine (single letter amino acid code A) and a substitution of glutamic acid (single letter amino acid code E) at residue 431 of SEQ ID NO:21 to an alanine. Other particularly suitable thrombin-thrombomodulin fusion proteins can have an amino acid sequence at least 80%, at least 85%, at least 90%, at least 91%, at least 92%, at least 93%, at least 94%, at least 95%, at least 96%, at least 97%, at least 98%, or at least 99% identical to SEQ ID NO:21, but which includes the WE thrombin double mutation (W to A substitution and E to A substitution as described herein).

The polypeptide of SEQ ID NO:21 can be treated with ecarin to remove amino acid residues 1-167 to form the final product representing the "active" thrombin-thrombomodulin fusion protein containing the thrombin domain and the thrombomodulin domain. SEQ ID NO:22 is a particularly suitable active thrombin-thrombomodulin fusion protein that includes the WE thrombin double mutation (W to A substitution at residue 262 of SEQ ID NO:22 and E to A substitution at residue 264 of SEQ ID NO:22).

Vector Constructs and Host Cells

In another aspect, the present disclosure is directed to a vector comprising a nucleic acid encoding a thrombin-thrombomodulin fusion protein, wherein the thrombin-thrombomodulin fusion protein comprises a thrombin domain and a thrombomodulin domain. Particularly suitable vector constructs are expression vector constructs.

The exact details of the vector construct vary according to the particular host cell that is to be used as well as to the desired characteristics of the expression system, as is well known in the art. For example, promoter sequences compatible with bacterial hosts are typically provided in plasmid vectors containing one or more convenient restriction sites for insertion of a contemplated nucleic acid segment. Suitable promoters and vectors include the Rec 7 promoter that is inducible by exogenously supplied nalidixic acid, JHEX25 (commercially available from Promega, Madison, Wis.) that is inducible by exogenously supplied isopropyl-β-D-thiogalacto-pyranoside (IPTG), tac (a hybrid of the trp and lac promoter/operator) present in plasmid vector pKK223-3 (commercially available from Pharmacia, Piscataway, N.J.) and is also inducible by exogenously supplied IPTG. Other suitable promoters and promoter/operators include the araB, trp, lac, gal, T7, and the like. For production in *S. cerevisiae*, the nucleic acid encoding a thrombin precursor of the disclosure is placed into operable linkage with a promoter that is operable in *S. cerevisiae* and which has the desired characteristics (e.g., inducible/derepressible or constituative), such as GAL1-10, PHOS5, PGK1, GDP1, PMA1, MET3, CUP1, GAP, TPI, MFα1 and MFα2, as well as the hybrid promoters PGK/α2, TPI/α2, GAP/GAL, PGK/GAL, GAP/ADH2, GAP/PHO5, ADH2/PHO5, CYC1/GRE, and PGK/ARE and other promoters known in the art. For a mammalian cell line, the promoter can be a viral promoter/enhancer (e.g., the herpes virus thymidine kinase (TK) promoter or a simian virus promoter (e.g., the SV40 early or late promoter) or the Adenovirus major late promoter, a long terminal repeat (LTR), such as the LTR from cytomegalovirus-(CMV), Rous sarcoma virus (RSV) or mouse mammary tumor virus (MMTV)) or a mammalian promoter, preferably an inducible promoter such as the metallothionein or glucocorticoid receptor promoters and the like.

Constructs can include additional nucleic acids appropriate for the intended host cell. For example, expression constructs for use in higher eukaryotic cell lines (e.g., vertebrate and insect cell lines) include a polyadenylation site and can include an intron (including signals for processing the intron), as the presence of an intron appears to increase mRNA export from the nucleus in many systems. Additionally, a secretion signal sequence operable in the host cell can be included as part of the construct. A particularly suitable secretion signal sequence can be a preprothrombin signal sequence. Other suitable secretion signal sequences can be obtained from human serum albumin, human prothrombin, human tissue plasminogen activator, and preproinsulin. Where the expression construct is intended for use in a prokaryotic cell, the expression construct can include a signal sequence that directs transport of the synthesized polypeptide into the periplasmic space or expression can be directed intracellularly. Constructs can also selectable markers for selecting host cells that contain the construct. Selectable markers are well known in the art. Marker genes contained in the expression vector for a microorganism can be, for example, an ampicillin resistance gene, tetracycline resistance gene for *E. coli* as a host; Leu2 gene for yeast as a host, and the like. Marker genes contained in the expression vector for an animal cell can be, for example, aminoglycoside 3'phosphotransferase (neo) gene, dihydrofolate reductase (dhfr) gene, glutamine synthetase (GS) gene, and the like.

In another aspect, the present disclosure is directed to a host cell comprising a vector, wherein the vector comprises a nucleic acid encoding a thrombin-thrombomodulin fusion protein that comprises a thrombin domain and a thrombomodulin domain.

Suitable host cells include, for example, eukaryotic host cells and prokaryotic host cells. Suitable eukaryotic cells include insect cells such as Sf9, and mammalian cell lines such as CHO, COS, 293, 293-EBNA, BHK, HeLa, NIH/

3T3, and the like. Exemplary yeast host cells include *Saccharomyces cerevisiae, Pichia pastoris, Hansenula polymorpha, Kluyveromyces lactis, Schwanniomyces occidentis, Schizosaccharomyces pombe* and *Yarrowia lipolytica*. Suitable prokaryotic cells are bacteria cells including, for example, *E. coli* cells such as, for example, BL21 (DE3), XL-1, TB1, JM103, BLR, pUC8, pUC9, pBR329, pPL and pKK223-3 cells and *Salmonella* such as, for examples, *S. typhi, S. typhimurium* and *S. typhimurium-E. coli* hybrids.

Methods for Preparing Thrombin-Thrombomodulin Fusion Proteins

Thrombin-thrombomodulin fusion proteins, thrombin domains, and thrombomodulin domains can be prepared by incorporating a nucleic acid encoding the thrombin-thrombomodulin fusion proteins, the thrombin domains, and/or the thrombomodulin domains into an expression vector, transforming suitable microorganism or animal cells with the resulting expression vector, and culturing the transformed microorganism or animal cells to produce the thrombin-thrombomodulin fusion proteins, the thrombin domains, and the thrombomodulin domains. For production of the thrombin domains and/or the thrombomodulin domains, a peptide synthesizer can also be used.

Nucleic acids encoding secretion signal sequences for secretion in microorganism or animal cell expression cultures can be included in the nucleic acid encoding the thrombin-thrombomodulin fusion proteins, the thrombin domains, and/or the thrombomodulin domains of the present disclosure so that the thrombin-thrombomodulin fusion proteins, the thrombin domains, and/or the thrombomodulin domains can be expressed and secreted into a culture medium. Suitable signal sequences include, for example, pel B signal; a factor signal; immunoglobulin signal SG-1, C25 signal, and the like. A particularly suitable secretion signal sequence is a factor V secretion peptide.

Sequences for tags can be included in a nucleic acid encoding the thrombin-thrombomodulin fusion proteins, the thrombin domains, and/or the thrombomodulin domains of the present disclosure. Suitable tags can be purification tags and labels. Suitable purification tags can be histidine tags and HPC4 tags.

Sequences encoding restriction sites can be included in a nucleic acid encoding the thrombin-thrombomodulin fusion proteins, the thrombin domains, and/or the thrombomodulin domains of the present disclosure. A particularly suitable restriction site can be a restriction site specific for cleavage by ecarin.

A variety of animal cells can be used as a host cell as described herein. A host cell can be transformed by any known methods including, for example, a calcium phosphate method, a DEAE dextran method, precipitation with e.g. lipid-based transfection reagents (e.g. lipofectin), fusion of protoplast with polyethylene glycol, electroporation, biolistic, and the like. A particularly suitable method for transfection is LIPOFECTAMINE® 3000.

Method for Measuring Protein C Activity Using Thrombin-Thrombomodulin Fusion Proteins In another aspect, the present disclosure is directed to a method for measuring protein C activity. In one embodiment, the method includes incubating a plasma sample with a thrombin-thrombomodulin fusion protein in a first reaction mixture; adding a substrate of activated protein C to the first reaction mixture to form a second reaction mixture; and analyzing the second reaction mixture.

In another embodiment, the method includes collecting an aliquot of the first reaction mixture; adding the aliquot to a substrate of activated protein C to form a second reaction mixture; and analyzing the second reaction mixture.

A particularly suitable amount of the thrombin-thrombomodulin fusion protein is about 0.1 nM. A particularly suitable amount of a protein C is about 100 nM. A particularly suitable amount of chromogenic substrate is about 50 µM.

In one embodiment, calcium is added to the first reaction mixture. In another embodiment, calcium is added to the second reaction mixture. A particularly suitable amount of calcium (as calcium chloride) is about 5 mM.

Any suitable method for analyzing the second reaction mixture can be used. Suitable methods can be, for example, measuring absorbance.

A suitable plasma sample can be a human plasma sample. A particularly suitable plasma sample is a citrated plasma sample. Other suitable plasma samples can be from animals such as, for example, primates, bovine, equine, mice, rats, rabbits, dogs, and cats.

Suitable protein C substrates are known to those skilled in the art. Particularly suitable protein C substrates can be, for example, SaPC-21 (commercially available from ANIARA, West Chester, Ohio), SPECTROZYME® PCa (commercially available Sekisui Diagnostics, Samford, Conn.), a chromogenic substrate H-D-Asp-Arg-Arg-p-nitroanilide (DRR) (described in Pozzi et al., Blood 2012; 120(3):664-670), 52366 (pyroGlu-Pro-Arg-p-nitroanilide), 52266 (H-D-Val-Leu-Arg-p-nitroanilide), BIOPHEN CS-21(66), Boc-Leu-Ser-Thr-Arg-7-amido-4-methylcoumarin (SEQ ID NO:23) (commercially available from SIGMA-ALDRICH, St. Louis, Mo.). Other suitable protein C substrates are described in Dang and Di Cera (Blood 1997; 89(6):2220-2222), which is incorporated herein by reference in its entirety.

Method for Measuring Protein C Activity Using Thrombin-Thrombomodulin Fusion Proteins In another aspect, the present disclosure is directed to a method for measuring protein C activity. The method includes contacting a plasma sample with a thrombin-thrombomodulin fusion protein and a phosphatide reagent to form a first reaction mixture; adding calcium to the first reaction mixture to form a second reaction mixture; and analyzing the second reaction mixture.

Any suitable method for analyzing the second reaction mixture can be used. Suitable methods can be, for example, measuring clotting time of the second reaction mixture, spectrophotometrically measuring the turbidity of the second reaction mixture, and combinations thereof.

A suitable plasma sample can be a human plasma sample. A particularly suitable plasma sample is a citrated plasma sample. Other suitable plasma samples are animal plasma samples.

Suitable phosphatide reagents can be, for example, ACTIN® and DADE® ACTIN® (commercially available from Siemens Healthcare Diagnostics, Inc., Tarrytown, N.Y.).

Method for Detecting Activated Protein C Resistant Factor Va

In another aspect, the present disclosure is directed to a method for detecting activated protein C resistant factor Va. The method includes contacting a plasma sample with a thrombin-thrombomodulin fusion protein; clotting the plasma by adding thromboplastin and $Ca^{2+}$; and measuring the clotting time.

The method can further include contacting a second plasma sample with PROTAC®; clotting the second plasma sample by adding thromboplastin and $Ca^{2+}$; and measuring the clotting time. In this step, it is known that PROTAC® activates protein C and factor V. In contrast, when the thrombin-thrombomodulin fusion protein is used, factor V is not activated to factor Va.

A suitable plasma sample can be a human plasma sample. A particularly suitable plasma sample is a citrated plasma sample. Other suitable plasma samples can be from animals such as, for example, primates, bovine, equine, mice, rats, rabbits, dogs, and cats.

Any suitable method for analyzing the second reaction mixture can be used. Suitable methods can be, for example, measuring clotting time of the second reaction mixture, spectrophotometrically measuring the turbidity of the second reaction mixture, and combinations thereof.

Methods for Activating Protein C Using Thrombin-Thrombomodulin Fusion Proteins

In another aspect, the present disclosure is directed to a method for activating protein C. The method includes contacting protein C with a thrombin-thrombomodulin fusion protein.

In one embodiment, the protein C can be a purified protein C. Purified protein C can be isolated from a blood source using protein extraction and purification methods. In another embodiment, the protein C can be a recombinant protein C.

Contacting the protein C with the thrombin-thrombomodulin fusion protein results in the conversion of the inactive zymogen protein C to active protein C (aPC). aPC can then proteolytically inactivate proteins factor Va and factor VIIIa. The aPC can also be used as an anticoagulant. Use of the thrombin-thrombomodulin fusion protein to convert protein C to aPC can avoid the risk of hazardous contamination arising from conversion of protein C to aPC using snake venoms. Additionally, the thrombin-thrombomodulin fusion protein presents a higher degree of selectivity since it does not activate factor V.

Kits

In another aspect, the present disclosure is directed to a kit for measuring protein C in plasma. The kit comprises a thrombin-thrombomodulin fusion protein and a protein C substrate, wherein the protein C substrate is specific for activated protein C.

Suitable protein C substrates and known in the art and described herein. A particularly suitable protein C substrate is chromogenic substrate H-D-Asp-Arg-Arg-p-nitroanilide (DRR).

The kits can further include instructions. Suitable instructions can be written instructions and instructions provided on an internet website.

In one embodiment, the instructions can describe a chromogenic method for measuring protein C in plasma. In another embodiment, the instructions can describe a clotting assay such as, for example an activated partial thromboplastin time (APTT) assay.

The disclosure will be more fully understood upon consideration of the following non-limiting Examples.

EXAMPLES

Example 1

Preparation of Thrombin-thrombomodulin Fusion Proteins

In this Example, the preparation of a DNA construct encoding thrombin-thrombomodulin fusion proteins is described.

A plasmid-encoding prethrombin-1 cDNA containing a factor V secretion peptide and a HPC4 purification epitope at the N-terminus served as starting genetic material. Using PCR, cDNA encoding soluble Epidermal Grown Factors or EGF domains of thrombomodulin (known as $TM_{456}$) was fused before the ending condon of the prethrombin 1 sequence. At the junction between prethrombin-1 and $TM_{456}$ different linkers containing repetitive sequences of glycine, serine and alanine residues were introduced. An additional restriction site for ecarin venom cleavage-activation was inserted into the prethrombin-1 cDNA for activation and purification purposes. DNA constructs were verified by DNA sequencing.

Example 2

In this Example, the expression of recombinant thrombin-thrombomodulin fusion proteins is described.

High-efficiency transfection of BHK cells with the plasmids prepared in Example 1 was achieved using Lipofectamine® 3000 reagent. Protein expression occurred in 1 Liter of DMEM supplemented with 5% calf bovine serum, 2 mM L-glutamine and 5 mL of penicillin (using 1000 Units stock). Expressed protein was secreted to the media after cleavage of factor V target peptide. Media was centrifuged, filtered and subjected directly to antibody-affinity chromatography with anti-HPC4 antibodies. A solution of 1M NaCl, 5 mM $CaCl_2$ and 20 mM Tris-Cl pH 7.4 was used to wash the column. After addition of a solution of 100 mM NaCl, 10 mM EDTA and 20 mM Tris-Cl pH 7.4, the proteins eluted as EDTA displaced the $Ca^{2+}$-antibody binding. The eluted fractions were dialyzed against a buffer containing 300 mM NaCl, 20 mM Tris-Cl pH 8.0. Addition of ecarin venom lead to formation of active enzymes. Finally, proteins were loaded onto a 5 mL Heparin-sepharose column and eluted with a linear gradient of 0.1-1 M NaCl.

Example 3

In this Example, the activation of protein C by thrombin-thrombomodulin fusion proteins was investigated.

The chromogenic assay BIOPHEN Protein C 2.5 was purchased from Hyphen BioMed (West Chester, Ohio) and the Protein C level in citrated plasma was measured using PROTAC® following the manufacturer's protocol. Results are shown in FIG. 1A. The same assay, with minor modifications, was repeated using thrombin-thrombomodulin fusion proteins in place of the PROTAC® enzyme. The results are shown in FIG. 1B. A direct comparison between the thrombin-thrombomodulin fusion protein and the PROTAC® enzyme activation is depicted in FIG. 1C. The thrombin-thrombomodulin fusion protein specifically activated Protein C in citrated plasma at a comparable rate as PROTAC®, but demonstrated an improved signal to noise ratio.

Example 4

In this Example, the activation of protein C by thrombin-thrombomodulin fusion proteins was investigated.

Thrombin-thrombomodulin fusion protein (0.1 nM) was added to a cell containing 50 μM of chromogenic substrates DRR, 100 nM protein C in the absence of external thrombomodulin under experimental conditions of 5 mM Tris, pH 7.4, 145 mM NaCl, 5 mM $CaCl_2$, 0.1% PEG 8000 at 37° C. Readings were done in a continuous assay at 405 nm. From the experimental curves, the values of kcat, km and Specificity (kcat/km) were calculated.

Example 5

In this Example, thrombin-thrombomodulin fusion proteins were monitored for enzyme-mediated conversion of protein C into activated protein C (aPC).

Purified thrombin-$TM_{456}$ fusion proteins and control thrombin were monitored for enzyme-mediated conversion of protein C into activated protein C (aPC) in the presence or absence of exogenous full-length thrombomodulin. Under control conditions with thrombin and absence of TM, minimal activated protein C (aPC) activity was generated in agreement with previous studies establishing that the low specificity of thrombin toward protein C in the absence of thrombomodulin resides in factors that limit the rate of formation of the thrombin-protein C complex. Addition of thrombomodulin served as a cofactor for an effective protein C activation augmenting the rate of cleavage with a specificity value of 220 $mM^{-1}s^{-1}$. Thrombin-$TM_{456}$ fusion proteins displayed a superior capability to cleave protein C in the absence of exogenous thrombomodulin that correlated with the length of the linkers. Linkers L31, L41, L55 and L69 were capable of enhancing approximately 1165-fold the activation rate of protein C and almost recapitulated the full kinetic activity displayed with thrombin and thrombomodulin separately. Enlargement of linkers favored protein C activation up to a maximum and further residues addition interfered with the enzymatic activity.

Example 6

In this Example, the cleavage of the procoagulant substrates fibrinogen and PAR1 by thrombin and thrombin-thrombomodulin fusion proteins was investigated.

Kinetics-HPLC coupled experiments were undertaken to compare the cleavage of thrombin and thrombin-thrombomodulin fusion proteins towards the procoagulant substrates fibrinogen and PAR1.

Thrombin-thrombomodulin fusion proteins displayed a lower amidolitic activity versus the procoagulant substrates, consistent with the occupancy of $TM_{456}$ to the exosite-1 of thrombin. The enhancement of protein C activation by the thrombin-thrombomodulin fusion proteins embraces the idea of the occupancy of exosite-I of thrombin by $TM_{456}$ establishing a competitive binding with PAR-1 and fibrinogen substrates which in turn would lead to a decrease in procoagulant activity.

In addition to the previous fibrinogen measurements determined in the coupled kinetic-HPLC assay, the fibrinogen activation was followed by studying the clotting curves. The time formation of the insoluble fibrin clot for the different constructs was evaluated by spectrophotometrically measuring the turbidity with time due to the light scattering produced by molecular aggregates. The clotting time for each curve was obtained from extrapolation of the slope to the zero absorbance baseline.

Thrombin rapidly triggered the fibrin formation within 5 minutes whereas addition of thrombomodulin at saturating concentrations delayed the clot formation up to 305 minutes. Similarly, the thrombin-thrombomodulin fusion proteins, L31 and L41, had slower fibrinogen activation (approximately 336 minutes) to a level comparable to the addition of thrombomodulin to thrombin to form the thrombin thrombomodulin complex.

As demonstrated herein, the thrombin-thrombomodulin fusion proteins of the present disclosure can be used to detect coagulopathies originated by an unproductive activation of the zymogen protein C. After the cleavage and release of the activation peptide, zymogen protein C is converted to the active anticoagulant active protein C (aPC). Such an activation process requires the perfect junction of the catalytic triad components formed by the substrate protein C, the enzyme thrombin and the cofactor thrombomodulin. The deficiency of any of the above mentioned components or specific punctual mutations in critical docking regions among them could eliminate the activation of protein C, hence triggering a coagulopathic state. When searching for the cause of a pro-coagulant state, especially in new-born, kits screening for protein C, are employed. One of the most common tests is designed to detect the presence and activation of protein C. The powerful venoms such as those from *Agkistrodon contrix* currently used in the kits activate protein C regardless of the presence of the physiological activators thrombin and thrombomodulin. Thus, enzyme extracted form snake venom can activate protein C even under conditions where the triad thrombin-thrombomodulin-protein C in vivo is not functional which can lead to the possibility of false negative results. In this case, the use of snake venoms to activate protein C, after bypassing thrombin and thrombomodulin to achieve protein C activation, would indicate normal activation of protein C (false negative). The use of the venom does not consider the possibility that the source of the procoagulant profile could come from specific mutations in the activation peptide of protein C that would impede the perfect docking between the components of the catalytic triad and further activation. In contrast, the thrombin-thrombomodulin fusion proteins of the present disclosure work similarly to the natural physiological activator (thrombin and thrombomodulin), and critical mutations affecting the correct docking of protein C-thrombin-thrombomodulin would result in an inefficient protein C cleavage that can be detected with the thrombin-thrombomodulin fusion proteins. Thus, the thrombin-thrombomodulin fusion proteins allow for illness detection in instances where snake venom-based tests result in a false negative. The specificity, safety and cost of the available tests would benefit from the use of the thrombin-thrombomodulin fusion proteins described herein.

These results demonstrated that the compositions and methods of the present disclosure can be used as anticoagulant therapies, activating protein C, and detecting coagulopathies.

What is claimed is:

1. A recombinant thrombin-thrombomodulin fusion protein comprising:
   a) a thrombin domain, wherein the thrombin domain is selected from the group consisting of a full-length thrombin polypeptide, a preprothrombin polypeptide, a prothrombin polypeptide, a prethrombin 1 polypeptide, a prethrombin 2 polypeptide, a thrombin A chain, a thrombin B chain, and combinations thereof, and wherein the full-length thrombin polypeptide is set forth in SEQ ID NO:3 or SEQ ID NO:5; and
   b) a thrombomodulin domain, wherein the thrombomodulin domain is selected from the group consisting of a full-length thrombomodulin protein and a thrombomodulin epidermal growth factor-like domain 456 (TM456), and wherein the thrombomodulin epidermal growth factor-like domain 456 (TM456) is set forth in SEQ ID NO:7 or SEQ ID NO:9.

2. The thrombin-thrombomodulin fusion protein of claim 1, wherein the thrombin domain is the full-length thrombin polypeptide having the amino acid sequence of SEQ ID NO:3.

3. The thrombin-thrombomodulin fusion protein of claim 1, wherein the thrombin domain further comprises an ecarin cleavage site.

4. The recombinant thrombin-thrombomodulin fusion protein of claim 1 further comprising a linker selected from the group consisting of SEQ ID NO:10, SEQ ID NO:11, SEQ ID NO:12, SEQ ID NO:13, SEQ ID NO:14, and SEQ ID NO:15.

* * * * *